Figure 1:
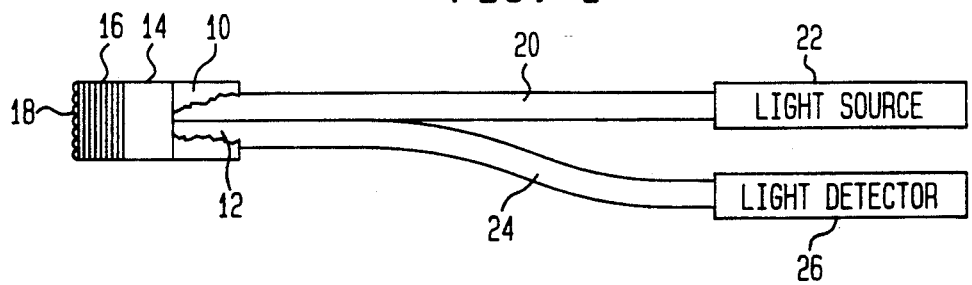

United States Patent [19]

Jelley et al.

[11] Patent Number: 5,107,316
[45] Date of Patent: Apr. 21, 1992

[54] CATOPTRICAL OPTO-ELECTRONIC GAS SENSOR

[75] Inventors: Kevin W. Jelley, Allentown, N.J.; Carl Colvard, Sunnyvale, Calif.

[73] Assignee: Siemens Corporate Research, Inc., Princeton, N.J.

[21] Appl. No.: 458,031

[22] Filed: Dec. 28, 1989

[51] Int. Cl.⁵ ................ H01L 31/0352; H01L 29/66
[52] U.S. Cl. ........................................ 357/25; 357/4; 357/30
[58] Field of Search ......................... 357/4, 16, 25, 30

[56] References Cited

U.S. PATENT DOCUMENTS

| | | | |
|---|---|---|---|
| 4,194,935 | 3/1980 | Dingle | 357/22 |
| 4,208,667 | 6/1980 | Chang et al. | 357/16 |
| 4,348,686 | 9/1982 | Esaki et al. | 357/30 |
| 4,450,463 | 5/1984 | Chin | 357/4 |
| 4,581,621 | 4/1986 | Reed | 357/12 |
| 4,620,214 | 10/1986 | Margalit et al. | 357/63 |
| 4,731,338 | 3/1988 | Ralston et al. | 437/22 |
| 4,745,452 | 5/1988 | Sollner | 357/30 |
| 4,931,851 | 6/1990 | Sibbald et al. | 357/25 |

OTHER PUBLICATIONS

"Tiny Electronic 'Noses' Promise Speedy Sensing", New York Times, Tuesday, Dec. 6, 1988.
"Quantum Well Makes New, High-Performance Optical Modulators", Thomas H. Wood, Laser Focus, Dec. 1986, pp. 121-124.
"Photocurrent response of GaInAs/InP multiple quantum well detectors . . . ", Temkin et al., Appl. Phys. Lett. 47(9), Nov. 1, 1985, pp. 978-980.
"A Dual-Mechanism Solid-State Carbon-Monoxide and Hydrogen Sensor . . . ", Jelley et al., IEEE Transactions on Electron Devices, vol. ED-34, No. 10, Oct. 87, pp. 2086-2097.
"Well size related limitations on maximum electroabsorption in . . . ", Jelley et al., Appl. Phys. Lett. 55(1), Jul. 3, 1989, pp. 70-72.
"High-Speed optical modulation with GaAs/GaAlAs quantum wells in a . . . ", Wood et al., Appl. Phys. Lett. 44(1), Jan. 1, 1984, pp. 16-18.
"Experimental Determination of Electroabsorption in . . . ", Jelley et al., Electronics Letter, Dec. 8, 1988, vol. 24, No. 25, pp. 1555-1557.
"High-contrast reflection modulation at normal incidence in asymmetric . . . ", Whitehead et al., Electronics Letters, Apr. 27, 1989, vol. 25, No. 9, pp. 566-568.

Primary Examiner—William D. Larkins
Attorney, Agent, or Firm—Adel A. Ahmed

[57] ABSTRACT

Apparatus for detecting the presence of a gas in an ambient atmosphere comprises a multiple quantum well structure; a thin layer of a transition metal formed on the multiple quantum well structure; and an arrangement for monitoring the transmission of electromagnetic radiation sent through the multiple quantum well structure and reflected back therethrough by the thin layer.

10 Claims, 1 Drawing Sheet

CATOPTRICAL OPTO-ELECTRONIC GAS SENSOR

The present invention relates to sensors for gases and, more particularly, to semiconductor sensors for sensing the presence of particular gases in the ambient atmosphere, such as a hydrogen component gas, utilizing a catoptrical or reflecting arrangement.

Sensors are known for detecting and signalling the presence of a gas by the effect of the gas on a semiconductor device. For example, a palladium-gate (Pd-gate) metal-oxide-semiconductor (MOS) structure sensitive to hydrogen gas is known. Such devices include a gate made of a transition metal, typically palladium in place of the conventional gate material generally utilized for an MOS device gate, such as aluminum or polysilicon. In a gas sensing device, the role of such a palladium gate structure is two-fold.

First, the gate acts as an electrode in contacting the device, and second, when exposed to hydrogen gas ($H_2$), the palladium gate surface acts as a catalyst in the dissociation of molecular hydrogen into atomic hydrogen, which is then adsorbed on the Pd surface. Some of the atomic hydrogen will diffuse through the bulk palladium and be adsorbed at the interface of the palladium and the silicon dioxide ($SiO_2$) layer which typically is deposited under the gate electrode. The adsorbed hydrogen both at the surface and at the interface is polarized and forms a dipole layer. The dipole layer at the interface causes a shift in the threshold voltage ($v_T$) of the MOS structure. The magnitude of the threshold shift due to the dipole layer is approximately proportional to the density of dipoles at the interface, which in turn is related to the concentration of hydrogen in the gas. It is also believed that a change in bulk hydrogen concentration also causes a shift in the work function, which will shift the threshold voltage.

Other gases such as hydrogen sulfide and ammonia have been sensed with a Pd-gate MOS structure. Gases such as carbon monoxide are adsorbed on the palladium surface but are too large molecularly to diffuse through the palladium bulk and therefore, give no response. Response to carbon monoxide has been obtained using a modified Pd gate in which holes from 1.5 to 3.0 $\mu m$ in diameter have been patterned through the palladium to permit the carbon monoxide to reach the palladium-silicon dioxide interface.

In a further development, an ultra-thin palladium film has been deposited as an array of small individual islands separated from each other by a distance on the order of a few Å to about 100 Å. The thickness of the film is kept below the point at which the islands tend to merge and, typically, may be in the order of 25 Å. Electrical contact between the individual island globules occurs as a result of electron tunnelling. An account of the foregoing technology is provided, for example, in the article "A Dual-Mechanism Solid-State Carbon-Monoxide and Hydrogen Sensor Utilizing and Ultrathin Layer of Palladium", by Kevin W. Jelley and G. Jordan Maclay, IEEE Transactions on Electron Devices, Vol. ED-34, No. 10; Oct. 1987.

Sensing of the shift in threshold voltage of the MOS device is typically performed by conventional electrical circuit arrangements. However, this requires connections to the MOS device, generally to the source and drain electrodes. It is herein recognized that the need for supply and sensing connections is a disadvantage, for example, in applications in which a sensor is located such that access has to be provided through gas-tight walls or glass windows.

In accordance with an aspect of the invention, a semiconductor device adapted for operation as a gas sensor, comprises a body of a semiconductor material including a substrate region and including a superlattice region over the substrate region. The superlattice region has first and second different materials arranged alternately in a plurality of parallel planar layers. The planar layers exhibit an absorption edge for electromagnetic radiation at a first wavelength thereof and have a respective predetermined relatively thin thickness dimension of a value wherein an electric field acting perpendicularly to the planar layers causes the absorption edge to shift to a second wavelength of the electromagnetic radiation. A layer of a transition metal is formed over the superlattice region, the layer of a transition metal having a relatively thin thickness dimension. Means are included for reflecting back electromagnetic radiation transmitted towards the layer of transition metal through the superlattice region.

In accordance with another aspect of the invention, the layer of a transition metal is sufficiently thick as to substantially reflect the electromagnetic radiation.

In accordance with still another aspect of the invention, the layer of a transition metal is sufficiently thin as to be substantially permeable to a gas.

In accordance with yet another aspect of the invention, the first material is aluminum gallium arsenide ($Al_xGa_{1-x}As$) and the second material is gallium arsenide (GaAs).

In accordance with still another aspect of the invention, the layer of a transition metal is of palladium.

In accordance with a further aspect of the invention, the electromagnetic radiation is light and fiber optic means is used for coupling light to and from the superlattice region.

In accordance with yet a further aspect of the invention, a method for detecting the presence of gas in an ambient atmosphere comprising the steps of:
transmitting electromagnetic radiation through a multiple quantum well structure for reflection by a thin mesh of a transition metal formed thereon;
exposing the mesh to the ambient atmosphere;
monitoring electromagnetic radiation returned by reflection through the multiple quantum well structure and the thin mesh for a change.

In accordance with still a further aspect of the invention, apparatus for detecting the presence of a gas in an ambient atmosphere comprises:
a multiple quantum well structure;
a thin layer of a transition metal formed on the multiple quantum well structure;
means for monitoring transmission of electromagnetic radiation sent through the multiple quantum well structure and reflected back by the layer.

In accordance with still a further aspect of the invention, apparatus for detecting the presence of a gas in an ambient atmosphere comprises a multiple quantum well structure; a thin layer of a transition metal formed on the multiple quantum well structure; and an arrangement for monitoring the transmission of electromagnetic radiation sent through the multiple quantum well structure and reflected back therethrough by the thin layer.

Figure 2:
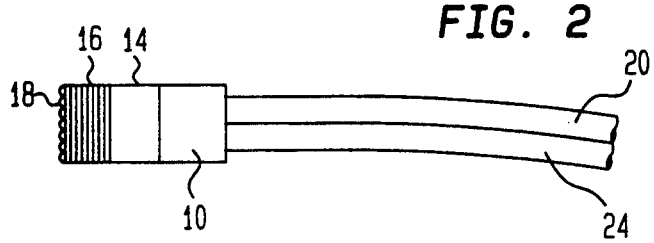
Figure 3:
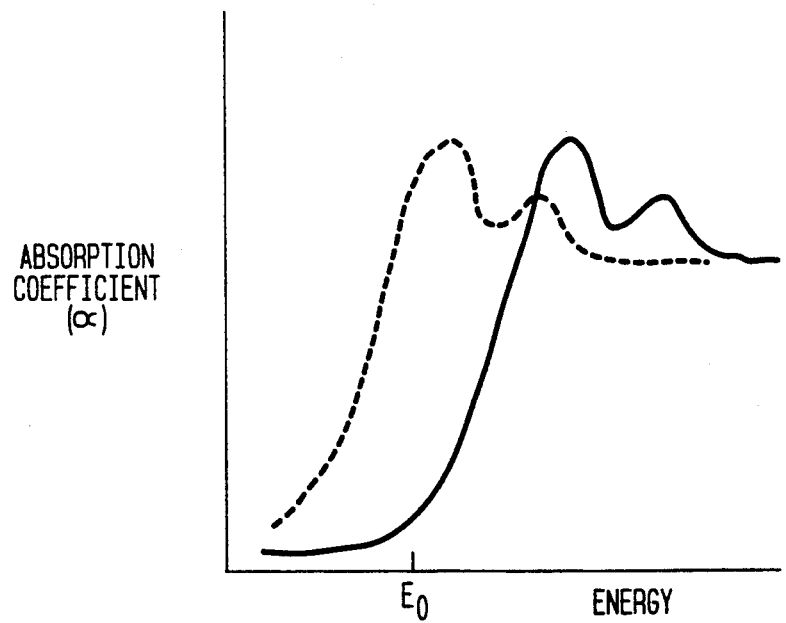
Figure 4:
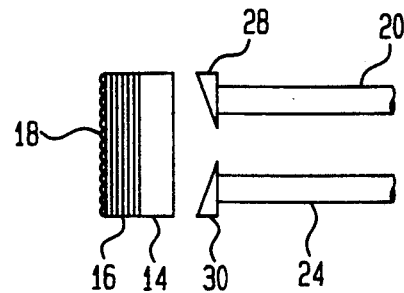

The invention will next be described in greater detail by way of an exemplatory embodiment and with the aid of the drawing in which FIGS. 1, 2 and 4 show embodiments of the invention, not to scale;

FIG. 3 is a graph, helpful in understanding the invention.

Referring to FIG. 1, a gallium arsenide substrate 10 is doped at a level in the order of $10^{20}$ cm$^{-3}$. Substrate 10 is opaque to electromagnetic radiation in the wavelength range of interest which is in the vicinity of 850 nanometers. Accordingly, a portion of substrate 10 is removed by etching so as to leave free a passage, generally indicated by reference numeral 12, around the center axis open for free passage of electromagnetic radiation, including light rays. Alternatively, substrate 10 can be made of a transparent substance such as indium gallium arsenide, as indicated in FIG. 2. Substrate 10 has formed thereon a region 14 of AlGaAs doped slightly less than the substrate, $10^{18}$ cm$^{-3}$. An undoped multiquantum well structure (MQW) 16 is formed over region 14. MQW 16 comprises a plurality of alternating layers of GaAs and AlGaAs, the layers being each in the order of 100 Å thick. A thin layer of a transition metal which may be palladium is formed over the topmost layer of MQW 16. Preferably, this topmost layer of MQW 15 is of AlGaAs, although this is not essential. The thickness of the layer of palladium is preferably in the order of 25 Å–50 Å for the detection of gases such as carbon monoxide; it can be made somewhat thicker for the detection of hydrogen containing gases. It is herein recognized that a palladium layer of such thin dimensions is typically discontinuous and on a microscopic scale comprises a mesh or matrix-like spread of individual islands. The layer of palladium is thus indicated schematically in FIG. 1 as a series of dots 18.

An optical fiber arrangement comprises a fiber 20 coupled to a light source 22, and a fiber 24 coupled to a light detector 26. Light from light source 22 passed through substrate 10, either by way of an opening through which fiber 20 passes as in FIG. 1, or through a transparent substrate as in FIG. 2. Thereafter, the light passed through MQW 16 and undergoes reflection at palladium layer 18. The reflected light is then transmitted by way of optical fiber 24 to light detector 26.

The characteristics of multiple quantum well structures such as MQW 16 are known. See the above referenced paper and, for example, the technical articles "Well size related limitations on maximum eletroabsorption in GaAs/AlGaAs multiple quantum well structures", K. W. Jelley et al., Appl. Phys. Lett. 55(1), 3 Jul. 1989; pp70-72; "High-speed optical modulation with GaAs/AlGaAs quantum wells in a p-i-n diode structure", T. H. Wood et al., Appl. Phys. Lett. 44(1), 1 Jan. 1984; "Experimental determination of electroabsorption in GaAs/Al$_{0.32}$Ga$_{0.68}$As multiple quantum well structures as function of well width", K. W. Jelley et al., Electronics Letters, 8th Dec. 1988, Vol. 24 No. 25 pp 1555-1557; "High-contrast reflection modulation at normal incidence in asymmetric multiple quantum well Fabry-Perot structure", M. Whitehead et al., Electronics Letters, 27th Apr. 1989, Vol. 25 No. 9, pp 566-568; and U.S. Pat. No. 4,731,338 (Ralston et al.), herein incorporated by reference.

Briefly, it is known that GaAs/AlGaAs quantum wells experience a shift to longer wavelengths in their absorption edge when acted upon by a perpendicular electric field. This is indicated schematically in FIG. 2 in which the solid line indicates the absorption coefficient without the presence of an electric field and the dashed line indicates the absorption coefficient under the action of an electric field.

In operation, light is transmitted through the structure and reflected back therethrough, as described so as to impinge on detector 26. A wavelength somewhat longer than 850 nanometers is selected so as to be passed by the GaAs whose absorption edge is at about 850 nanometers. Palladium layer 18 is then exposed to an atmosphere in which hydrogen may be present which it is desired to detect.

As has been earlier mentioned, it is known that when exposed to hydrogen gas (H$_2$), the palladium surface acts as a catalyst in the dissociation of molecular hydrogen into atomic hydrogen, which is then adsorbed on the Pd surface. Some of the atomic hydrogen will diffuse through the interstices in the palladium mesh and be adsorbed at the surface of the topmost layer of MQW 16. In the event palladium layer 18 is somewhat thicker, the atomic hydrogen will diffuse through it and be adsorbed at the palladium GaAs interface. The adsorbed hydrogen at the surface is polarized and forms a dipole layer. The dipole layer at the surface results in the effect of a bias being applied to palladium layer 18, which causes an electric field to act on MQW 16. The high level of doping in layer 14 and in substrate 10 will tend to restrict the resulting electric field to MQW 16 and thus maximize its effect. The electric field then causes the absorption edge to shift to a longer wavelength, as indicated in FIG. 3.

If the transmitted/reflected light being monitored is of the correct wavelength, it will now fall within the shifted absorption edge and detector 20 will register a drop in intensity and thereby indicate the presence of hydrogen. Naturally, the greater the concentration of hydrogen in the atmosphere to which the layer 18 is exposed, the greater the shift, so that the extent to which light is absorbed or transmitted provides a quantitative measure of the concentration of hydrogen in the ambient atmosphere.

Referring now to FIG. 4, fibers 20 and 24 are shown to be optically coupled to substrate 14 by way of prisms 28 and 30, respectively. The angles of prisms 28 and 30 are selected so as to cause the light in each case to make an angle with the plane of substrate 10 equal to the Brewster angle. If the light is polarized parallel to the plane of incidence, it is wholly transmitted, i.e. without reflections. This is clearly advantageous in maximizing the useful signal.

While the above exemplatory embodiments utilize fiber optics, this is not essential to the invention. With appropriate operating conditions, it is possible to transmit an illuminating beam onto substrate 10 and to recover the return signal by means of a telescope, for example, thereby avoiding all need for a physical connection to the sensor.

With all of the described embodiments, the advantage is gained of having the light signal traverse MQW 16 twice and thereby realize a gain in sensitivity to a given change in absorption.

The invention has been described by way of illustrative embodiments. Various changes are possible which will be apparent to one skilled in the art. For example, other materials can be used for the detection of other gases. For another example, light can be transmitted in either direction for monitoring of the absorption edge change. Such and similar changes and modifications do not depart from the spirit and scope of the invention which is intended to be limited only by the claims following.

We claim:

1. A semiconductor device adapted for operation as a gas sensor, comprising:
    a body of a semiconductor material including a substrate region and including a superlattice region over said substrate region, said superlattice region having first and second different materials arranged alternately in a plurality of parallel planar layers, said planar layers exhibiting an absorption edge for electromagnetic radiation at a first wavelength thereof and having a respective predetermined relatively thin thickness dimension of a value wherein an electric field acting perpendicularly to said planar layers causes said absorption edge to shift to a second wavelength of said electromagnetic radiation;
    a layer of a transition metal over said superlattice region, said layer of a transition metal having a relatively thin thickness dimension and being sufficiently thin so as to be substantially permeable to a gas; and
    means for reflecting back electromagnetic radiation transmitted towards said layer of transition metal through said superlattice region.

2. A semiconductor device is recited in claim 1, wherein said layer of a transition metal is sufficiently thick as to substantially reflect said electomagnetic radiation.

3. A semiconductor device as recited in claim 1, wherein said first material is aluminum gallium arsenide ($Al_xGaAs_{1-x}$) and said second material is gallium arsenide (GaAs).

4. A semiconductor device as recited in claim 3, wherein said layer of a transition metal is of palladium.

5. A semiconductor device as recited in claim 1, wherein said substrate region has at least a portion thereof removed for providing a clear passage for said electromagnetic radiation.

6. A semiconductor device as recited in claim 4, wherein said substrate region has at least a portion thereof removed for providing a clear passage for said electromagnetic radiation.

7. A semiconductor device as recited in claim 4, wherein said layer of a transition metal is formed on a final layer of said superlattice region, said final layer being of aluminum gallium arsenide.

8. A semiconductor device as recited in claim 1, wherein said electromagnetic radiation is light, including fiber optic means for coupling light to and from said superlattice region.

9. A semiconductor device as recited in claim 8, wherein said fiber optic means comprises a fiber for incoming light and a fiber for outgoing light.

10. A semiconductor device as recited in claim 8, wherein said light is coupled to an interface at the Brewster angle.

* * * * *